United States Patent [19]

Figura

[11] 4,166,394

[45] Sep. 4, 1979

[54] METHOD FOR TEMPERATURE COMPENSATION OF AN ULTRASONIC MEASURING DEVICE OF THE CONCENTRATION OF SOLUTIONS AND CIRCUIT ARRANGEMENT FOR ITS EXECUTION

[75] Inventor: Zdenko Figura, Bosaca, Czechoslovakia

[73] Assignee: Vyskumny ustav mechanizacie a automatizacie, Nove Mesto nad Vahom, Czechoslovakia

[21] Appl. No.: 808,911

[22] Filed: Jun. 22, 1977

[30] Foreign Application Priority Data

Jun. 30, 1976 [CS] Czechoslovakia ................... 4301-76

[51] Int. Cl.$^2$ .......................................... G01N 29/02
[52] U.S. Cl. ................................................... 73/597
[58] Field of Search ................... 73/560, 67.5 R, 597; 340/3 E, 5 S

[56] References Cited

U.S. PATENT DOCUMENTS

| | | | |
|---|---|---|---|
| 3,076,519 | 2/1963 | Alsabrook | 340/3 E |
| 3,299,707 | 1/1967 | Noel | 340/5 S |
| 3,973,430 | 8/1976 | Cirulis et al. | 73/560 |

OTHER PUBLICATIONS

Chen et al., "Three-Transducer Differential Phase Shift Method for Measurement of Ultrasonic Velocity in Liquid", Review of Scientific Instruments, pp. 1095–1098, 8/1975.

*Primary Examiner*—Stephen A. Kreitman

[57] ABSTRACT

The temperature compensation of an ultrasonic measuring device of the concentration of solutions is achieved by application of a reference solution with a maximum speed of propagation of ultrasonic waves and a reference solution with a minimum speed of propagation of ultrasonic waves, by determining differences of time intervals of the speed of propagation of ultrasonic waves of these reference solutions with respect to the measured solution and by dividing the resulting differences.

3 Claims, 2 Drawing Figures

METHOD FOR TEMPERATURE COMPENSATION OF AN ULTRASONIC MEASURING DEVICE OF THE CONCENTRATION OF SOLUTIONS AND CIRCUIT ARRANGEMENT FOR ITS EXECUTION

BACKGROUND OF THE INVENTION

The measuring of concentration of materials and a subsequent regulation of the concentration to a required value is an important operation for all kinds of chemical manufacture. The ultrasonic measuring device possesses properties which adapt it for application in automatic regulating circuits as a pick-up device. The probe of the apparatus can be situated directly in the investigated liquid. It requires no attendance and operates automatically by the impulse method with a high repeating frequency so that it yields practically continuous information about conditions of the investigated medium. The dependence of the speed of propagation of ultrasonic waves in the liquid on its composition-on its concentration is thereby utilized for measurements. The dependence of the speed of propagation on temperature is linear for most liquids up to critical temperatures.

Two main types of temperature dependent ultrasonic propagation variations for different concentrations of some material are known. The first type of dependence on temperature for a certain concentration of the investigated material is the simpler of these, as the individual straight lines of a resulting graph are parallel as, for instance, for aqueous solutions of $H_2SO_4$, NaOH, glycerol and others. The line slopes for the second type of dependence are different for each concentration of a certain solution. The temperature dependence usually changes its sign within a relatively narrow extent of concentration, for instance, with nitric acid 20–30%, ammonia, water, and others.

The compensation of the influence of temperature on solutions having the first type of dependence is accomplished in different ways. There are known methods based on measurements of temperature and on introduction of corrections to the output signal which are proportional to variations of temperature. Another method utilizes, for the determination of the concentration of the solution, a reference solution maintained at the same temperature as the measured solution. The difference of time intervals corresponding to the difference of the speed of sound propagation in both solutions is constant with variations of temperature, and changes only in case of a change of concentration.

These methods, however, cannot be applied for measuring the concentration of solutions of the second type of dependence due to variation of the line slope.

SUMMARY OF THE INVENTION

It is an object of this invention to provide the compensation of ultrasonic measuring devices of concentration of solutions even for solutions of the second type of dependence. It is another object of this invention to provide a practically continuous control of the concentration in the course of different technological processes. According to this invention, differences are determined between time intervals obtained due to the speed of propagation of ultrasonic waves in a measured solution and in a lower reference solution with a minimum speed of propagation of ultrasonic waves and between the lower reference solution and an upper reference solution having a maximum speed of propagation of ultrasonic waves. These differences are subsequently mutually divided. According to another feature of the invention, the probe in the measured liquid is connected to the input of a first difference circuit. The probe of the lower reference solution is connected to the input of the first difference circuit and to the input of a second difference circuit. The feeler of the upper reference solution is connected to the input of the second difference circuit. The output of the first difference circuit is connected to the input of a first transducer of the time interval to voltage, and the output of the second difference circuit is connected to the input of a second transducer of the time interval to voltage. The output of the first transducer of the time interval and the output of the second transducer of the time interval are connected to inputs of a proportionality circuit. The output from the proportionality circuit is connected to a measuring apparatus.

An advantage of the method and circuit arrangement for compensation of the influence of temperature according to this invention is that it also compensates for the influence of temperature for solutions with the second type of dependence on temperature. Another advantage is that this kind of compensation can also be used, without alterations, for solutions with the first type of dependence on temperature.

BRIEF DESCRIPTION OF THE DRAWING

An exemplary circuit arrangement for execution of the method according to this invention is shown in
FIG. 1 of the attached drawing.

DETAILED DESCRIPTION OF A PREFERRED EMBODIMENT

Figure 1:
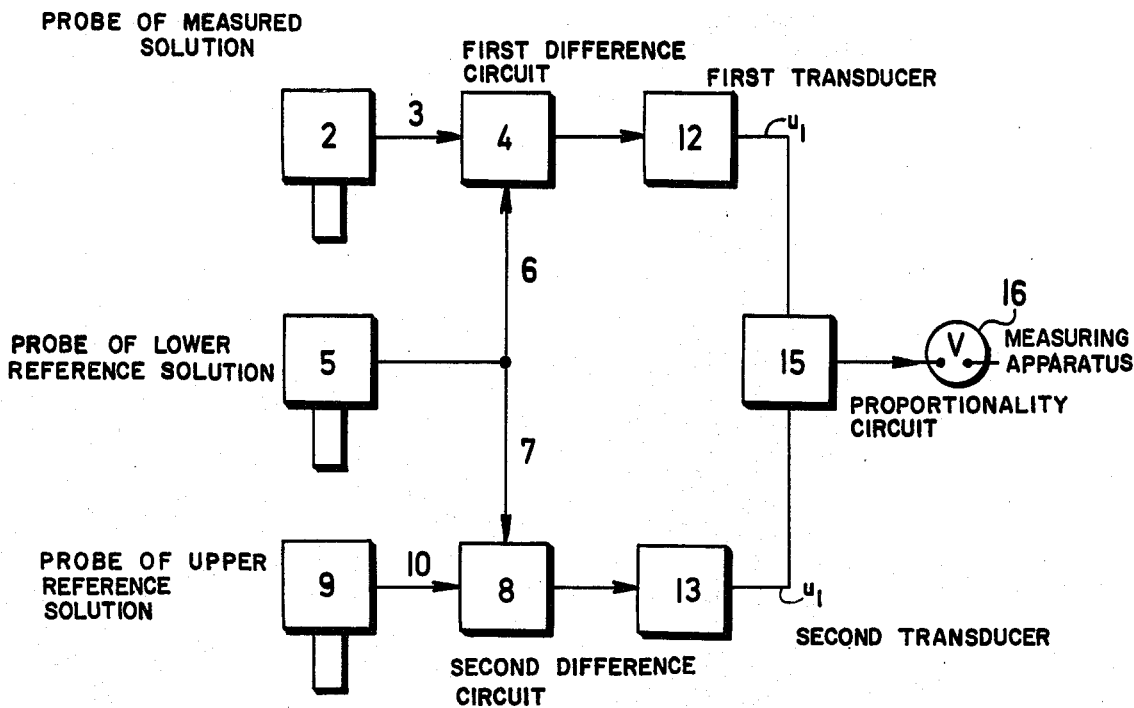

The circuit arrangement for temperature compensation of an ultrasonic measuring device of the concentration of solutions as shown in the drawing comprises a probe 2 of the measured solution, connected to the input 3 of a first difference circuit 4. A probe 5 of a lower reference solution is connected to the input 6 of circuit 4 and to an input 7 of a second difference circuit 8. A probe 9 of an upper reference solution, is connected to the input 10 of the circuit 8, whereby the output of the circuit 4 is connected to the input of a first transducer 12 of the time interval to voltage. The output of circuit 8 is connected to the input of a second transducer 13 of the time interval to voltage, the output of which is connected to the input of a proportionality circuit 15. The output from transducer 12 is similarly connected to the input of the proportionality circuit 15. The output from circuit 15 is connected to a measuring apparatus 16.

Figure 2:
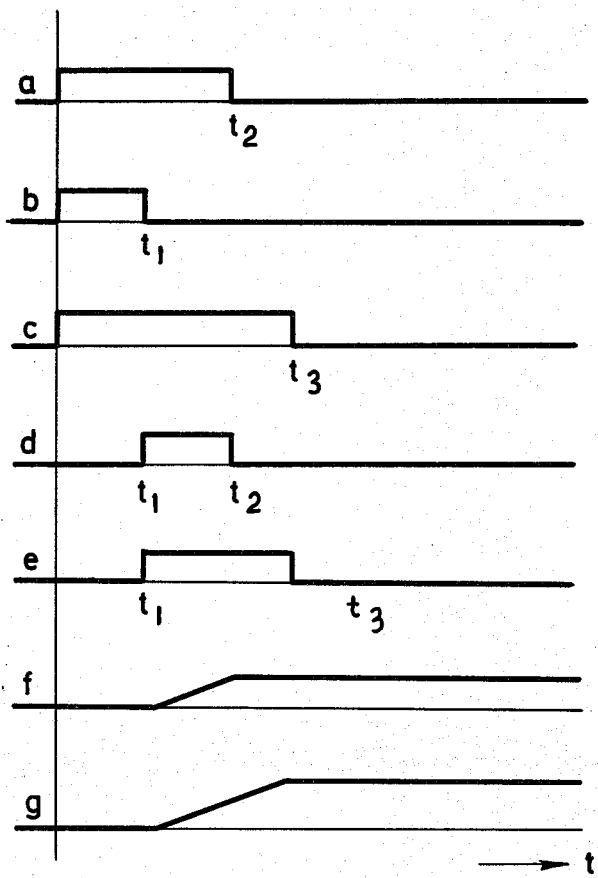
FIG. 2 shows the waveforms of electric signals of different circuits.

In operation, impulses are supplied by the probe 25 and 9. The length of these impulses corresponds to the time of propagation of the ultrasonic impulse according to waveforms a, b, c (see FIG. 2). A difference between the length of duration of the impulse from the probe 5 (from the lower reference solution) and from the probe 2 (from the measured solution) is determined by the first difference circuit 4 so that circuit 4 provides at its output the impulse difference according to waveform d. A difference between the length of duration of the impulse from the probe 2 and from the probe 9 is determined similarly in the second difference circuit 15 which provides at its output the impulse difference according to waveform e.

An operation by way of integration is performed in the first transducer 6. Similarly transducer 13 provides an output according to waveforms f and g so that we obtain on the output corresponding voltages $u_1$ and $u_2$. An analog division operation is performed in (proportionality) circuit 15 so that we obtain on its output a standard unidirectional voltage measured by the measuring apparatus 16. Apparatus 16 shows, for a concentration of the measured solution identical with the concentration of the reference solution with a minimum speed of propagation, a zero deflection. For a concentration of the measured solution identical with the concentration of the reference solution with a maximum speed of propagation apparatus 16 shows a maximum deflection.

Although the invention is illustrated and described with reference to one preferred embodiment thereof, it is to be expressly understood that it is in no way limited to the disclosure of such a preferred embodiment, but is capable of numerous modifications within the scope of the appended claims.

What is claimed is:

1. A method for temperature compensation of an ultrasonic measuring device of the concentration of solutions, said method comprising the steps of determining the difference between time intervals obtained due to the speed of propagation of ultrasonic waves in a measured liquid with respect to a first reference liquid with a minimum speed of propagation of ultrasonic waves, determining the difference between time intervals obtained due to the speed of propagation of ultrasonic waves in said first reference liquid with respect to a further reference liquid having a maximum speed of propagation of ultrasonic waves, and by subsequently dividing these difference values.

2. Circuit arrangement for temperature compensation of an ultrasonic measuring device of the concentration of measured solutions comprising in combination; a measured solution, a first reference solution with a minimum speed of propagation of ultrasonic waves, a second reference liquid with a maximum speed of propagation of ultrasonic waves, probes determining the speed of propagation of ultrasonic waves in each of said measured solution and said first and second reference solutions, a first and a second difference circuit adapted to determine differences of speeds of propagation of ultrasonic waves in different solutions, a first and a second transducer of a time interval to voltage transducer, a proportionality circuit adapted to determine the proportion of voltages from both transducers and a measuring apparatus for measuring this value, the probe of the measured solution connected to the input of the first difference circuit, the probe of the first reference solution connected to the input of the first difference circuit and to the input of the second difference circuit, the probe of the second reference solution connected to the input of the second difference circuit, the output of the first difference circuit being connected to the input of the first transducer, the output of the second difference circuit connected to the input of the second transducer, the output of both said transducers connected to inputs of the proportionality circuit, the outputs of this proportionality circuit connected to the measuring apparatus.

3. A circuit for temperature compensation of the concentration of a measured solution responsive to ultrasonic waves applied to said solution, said circuit comprising first, second and third probes for determining the speed of ultrasonic waves in said measured solution and first and second reference solutions, said circuit also including first and second difference circuits for indicating the difference in speeds of propagation of ultrasonic waves in said measured and first solutions and in said measured and second solutions, and means for measuring the ratio of said differences.

* * * * *